(12) United States Patent
Crivello et al.

(10) Patent No.: US 8,747,109 B2
(45) Date of Patent: Jun. 10, 2014

(54) DENTAL APPLIANCES AND METHODS FOR THEIR FABRICATION

(76) Inventors: James V. Crivello, Clifton Park, NY (US); Lewis R. Morrison, Clifton Park, NY (US)

( * ) Notice: Subject to any disclaimer, the term of this patent is extended or adjusted under 35 U.S.C. 154(b) by 0 days.

(21) Appl. No.: 13/407,949

(22) Filed: Feb. 29, 2012

(65) Prior Publication Data

US 2012/0225402 A1  Sep. 6, 2012

Related U.S. Application Data

(60) Provisional application No. 61/449,293, filed on Mar. 4, 2011.

(51) Int. Cl.
| | | |
|---|---|---|
| *A61C 9/00* | (2006.01) | |
| *A61P 31/04* | (2006.01) | |
| *A61K 8/895* | (2006.01) | |
| *A61Q 11/00* | (2006.01) | |

(52) U.S. Cl.
USPC ............ 433/37; 424/78.37; 424/49; 523/105

(58) Field of Classification Search
None
See application file for complete search history.

(56) References Cited

U.S. PATENT DOCUMENTS

| 5,403,885 | A | * | 4/1995 | Voigt et al. ................ 524/731 |
| 5,536,168 | A | | 7/1996 | Bourke |
| 5,816,255 | A | | 10/1998 | Fishman et al. |
| 7,305,990 | B2 | | 12/2007 | Mathias |
| 7,530,355 | B2 | | 5/2009 | Berghash |
| 7,607,438 | B2 | | 10/2009 | Pelerin |
| 2007/0134618 | A1 | | 6/2007 | Hare |
| 2008/0200584 | A1 | * | 8/2008 | Bottcher et al. ........... 523/109 |

FOREIGN PATENT DOCUMENTS

| EP | 0 522 341 A1 | | 1/1993 |
| EP | 1741420 | * | 1/2007 |
| EP | 2266528 | * | 12/2010 |
| WO | WO 93/17654 | * | 9/1993 |
| WO | WO 93/017654 A1 | | 9/1993 |

OTHER PUBLICATIONS

Hanse chemie AG, Technical data sheet: "Dental impression materials and bite registrations with silicone base materials"; downloaded on Jan. 20, 2011 from http://hanse-chemie.ag/index.php?id=57&L=2.

* cited by examiner

*Primary Examiner* — Anoop Singh
*Assistant Examiner* — Anna Falkowitz
(74) *Attorney, Agent, or Firm* — Heslin Rothenberg Farley & Mesiti P.C.

(57) ABSTRACT

The invention consists of a rapidly crosslinkable, two-component silicone elastomer together with a specially designed tray that serves as a form for the silicone resin and forms an integral portion of a dental appliance.

6 Claims, 2 Drawing Sheets

1A

1B

2A

2B

DENTAL APPLIANCES AND METHODS FOR THEIR FABRICATION

CROSS REFERENCE TO RELATED APPLICATION

This application claims the benefit of U.S. provisional application Ser. No. 61/449,293, filed Mar. 4, 2011, entitled "NOVEL DENTAL APPLIANCES AND METHODS FOR THEIR FABRICATION", the entirety of which is incorporated herein by reference.

TECHNICAL FIELD

The present invention is directed towards new materials and processes used in the fabrication of dental appliances such as night guards for the mitigation of the effects of bruxism (teeth grinding), mouth guards to prevent injury during sporting and other athletic activities and trays for teeth whitening. Specifically, the invention is intended to provide a dental appliance with a material that will readily conform to the contours of the mouth and teeth of patients and will set rapidly to give a durable, well-fitting, comfortable elastomeric dental appliance that can be repeatedly withdrawn and reinserted many times for extended use. The invention further consists of a rapidly crosslinkable, two component silicone elastomer together with a specially designed tray that serves as a form for the silicone resin before and during cure and, in addition, forms an integral portion of the completed dental appliance.

BACKGROUND INFORMATION

There is a general need for dental appliances that can be specifically tailored to an individual patient, that can be fabricated within a short time during a single patient visit and that are durable and comfortable to use even after repeated insertion and removal from the oral cavity. A number of appliances are in current use in dentistry, but none provide the combination of characteristics described above. For example, commercially available night guards are designed to be worn while sleeping. The guards mitigate the effects of involuntary grinding on the teeth and the associated oral tissues and structures. In addition, the guards provide relief in some patients from headaches and jaw pain that result from teeth grinding. Generally, these devices consist of a low glass transition thermoplastic elastomer that is contained within a molded thermoplastic tray. The tray may be rigid or flexible but should have a higher glass transition temperature than the thermoplastic elastomer that it holds. The patient places this appliance briefly in boiling water and then inserts it into the mouth, biting down to impress and conform the thermoplastic elastomer to the teeth. On cooling, the impression is preserved.

The results obtained using such technology leave much to be desired. First, insertion of a hot device into the mouth always carries considerable risk of injury. Second, the results and utility of the appliance depend on upon many variables including how well the patient positions the device and how much pressure is applied during the bite down portion of the process. Further, the flow of the thermoplastic material during the above process is very limited, such that only portions of the teeth are encapsulated; this results in a loose and ill-fitting appliance. These negative factors result in poor patient use compliance and a corresponding unsatisfactory relief of the symptoms of teeth grinding. Considerably more expensive but better fitting night guards can be fabricated by an impression-casting process as described below for sporting mouth guards.

Two methods are used in the fabrication of mouth guards used to protect teeth during sporting or other activities. They can be made by the so-called "boil and bite" process described above for night guards. In addition, these guards can be fabricated by taking a dental impression by licensed dental personnel, followed by making a cast model from the impression and then forming the final mouth guard around this casting. This normally requires two visits by the patient to a dental office as well as several days for completion of the entire process. Further, the long, complicated, multistep process required for the fabrication adds significantly to the overall cost of the resulting appliance. There are some modifications of this technique whereby sports mouth guards are made by having the athlete take his own impression and then fabricating the mouth guard in a laboratory. This reduces the cost somewhat. A greatly simplified one-step, rapid, low cost process would be highly desirable.

Bleaching agents are commonly used to whiten teeth. To afford an even, cosmetically attractive whitening process over all the targeted teeth, it is desirable to find some method in which the bleaching agent can be applied uniformly. During the bleaching process, it would be advantageous to isolate the teeth undergoing whitening within the oral cavity since the process may require several minutes to several hours for completion. In such instances, it is further desirable to limit the potential ingestion of bleaching agents by the patient as well as the exposure of dental tissues to these agents. In some cases, the bleaching agents are applied to the teeth and, thereafter, the bleaching action is aided by the exposure to UV light.

Periodontal disease, popularly called gingivitis, is present to varying degrees in approximately 85% of the population. In severe cases this bacterial disease results in serious infections of the gums with accompanying soreness and bleeding and may eventually lead to erosion of the teeth below the gum line and their subsequent loss. Treatments for periodontal disease include antibacterial agents that kill bacteria responsible for periodontal disease on contact and oxidizing agents that remove the protective bacterial biofilm formed on teeth and gums that promotes bacterial reinfection. The devices of this invention can be employed in two ways to mitigate the effects of periodontal disease. Custom fit trays can be readily, quickly and inexpensively constructed using the technology described herein. These trays can be filled with antibacterial and/or oxidizing agents.

Certain common requirements are necessary to successfully address all of the above targeted dental appliances and other applications. First, the materials employed must possess no appreciable oral or dermal toxicity. They should be odorless and tasteless and should provide no permanent bonding to oral tissues or teeth. They should release easily and cleanly from those tissues and teeth to preserve fine details and fit of the dental appliance. The materials should be compatible with water and saliva as well as other agents commonly found in oral fluids and should undergo no appreciable degradation in the presence of those agents. Silicones, i.e. poly(dimethylsiloxanes), possess all of these properties and are, therefore, the favored materials of choice for such applications. However, commercially available crosslinkable silicones currently used in dentistry, specifically in dental impressions, are not suitable for the above applications since they both have unacceptably long cure times and possess poor mechanical properties, especially poor tear strength. For the above described applications, it is desirable to have cure times under fifteen minutes and, ideally, under seven minutes at physiological temperatures (approx. 37° C.) and high tear strengths that allow repeated removal and reinsertion of the dental appliance. In addition, the silicone elastomer produced should be tough and possess sufficient stiffness to resist bite-through by the patient while at the same time being soft and compliant for comfortable long-term wear. Prior to cure, the silicone should possess a sufficiently high viscosity so that the resin does not flow appreciably during application and cure.

Currently, the above described requirements are not met by any existing material, silicone or otherwise. It is also recognized that a crosslinkable silicone material by itself is not usually sufficient for the fabrication of a workable dental appliance. Commonly, the device will consist of a combination of a crosslinkable silicone together with a silicone curing tray that becomes an integral portion of the resulting finished dental appliance.

SUMMARY OF THE INVENTION

The present invention addresses the requirements listed above by satisfying the need for safe, reusable, comfortable, easily applied dental appliances. In accordance with the above, it is an object of the present invention to provide dental appliances with these characteristics. This invention consists of 1) a novel, two-component platinum-catalyzed crosslinkable silicone resin together with 2) a specially designed tray.

One embodiment of the present invention relates to a kit for preparing a dental appliance comprising:
  a. a tray insertable into the mouth of a subject; and
  b. a two-part prepolymer mixture, substantially free of surfactant, said mixture comprising:
    (1) a first component comprising
      (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said first component; and
      (ii) a platinum catalyst; and
    (2) a second component comprising
      (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said second component; and
      (ii) a linear, branched or cyclic hydrofunctional poly(siloxane) having a Si—H content from 1.4 to 5.0 mmol/g and viscosity of 40-300 cps;
  said cross-linkable, vinyl-functional poly(dimethylsiloxane)s being substantially free of monomers containing quaternary silicon-oxygen bonded repeat units.

The present invention provides, in a second aspect, a resin substantially free of surfactant comprising:
  (a) a first component comprising
    (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said first component; and
    (ii) a platinum catalyst;
  (b) a second component comprising
    (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said second component; and
    (ii) a linear, branched or cyclic hydrofunctional poly(siloxane) having a Si—H content from 1.4 to 5.0 mmol/g and viscosity of 40-300 cps;
  said cross-linkable, vinyl-functional poly(dimethylsiloxane)s being substantially free of monomers containing quaternary silicon-oxygen bonded repeat units.

In a third aspect, the present invention provides a method of making a dental appliance comprising:
  a. providing a tray insertable into the mouth of a subject; and
  b. mixing a two-part prepolymer mixture, substantially free of surfactant, said mixture comprising:
    (1) a first component comprising
      (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said first component; and
      (ii) a platinum catalyst;
    (2) a second component comprising
      (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said second component; and
      (ii) a linear, branched or cyclic hydrofunctional poly(siloxane) having a Si—H content from 1.4 to 5.0 mmol/g and viscosity of 40-300 cps;
  said cross-linkable, vinyl-functional poly(dimethylsiloxane)s being substantially free of monomers containing quaternary silicon-oxygen bonded repeat units,
  wherein said two-part prepolymer mixture is either mixed in said tray or mixed separately and introduced into said tray as a mixture.

In a fourth aspect, the present invention provides a dental appliance comprising:
  (a) a tray; and
  (b) a polymer formed by reacting a two-part prepolymer mixture, substantially free of surfactant, said mixture comprising:
    (1) a first component comprising
      (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said first component; and
      (ii) a platinum catalyst; and
    (2) a second component comprising
      (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said second component; and
      (ii) a linear, branched or cyclic hydrofunctional poly(siloxane) having a Si—H content from 1.4 to 5.0 mmol/g and viscosity of 40-300 cps;
  said cross-linkable, vinyl-functional poly(dimethylsiloxane)s being substantially free of monomers containing quaternary silicon-oxygen bonded repeat units.

The present invention provides, in a fifth aspect, a two-part resin kit comprising:

(a) a first component comprising
  (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said first component; and
  (ii) a platinum catalyst;
(b) a second component comprising
  (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said second component; and
  (ii) a linear, branched or cyclic hydrofunctional poly(siloxane) having a Si—H content from 1.4 to 5.0 mmol/g and viscosity of 40-300 cps;
said cross-linkable, vinyl-functional poly(dimethylsiloxane)s being substantially free of monomers containing quaternary silicon-oxygen bonded repeat units, and
said resin being substantially free of surfactant.

These, and other objects, features and advantages of this invention will become apparent from the following detailed description of the various aspects of the invention taken in conjunction with the accompanying drawings.

BRIEF DESCRIPTION OF THE DRAWINGS

FIG. 1A shows a tray without a tab for insertion and removal. FIG. 1B shows a tray with tabs for insertion and removal.

FIG. 2A shows a tray without a tab for insertion and removal. FIG. 2B shows a tray with tabs for insertion and removal.

DETAILED DESCRIPTION OF THE INVENTION

Figure 1:
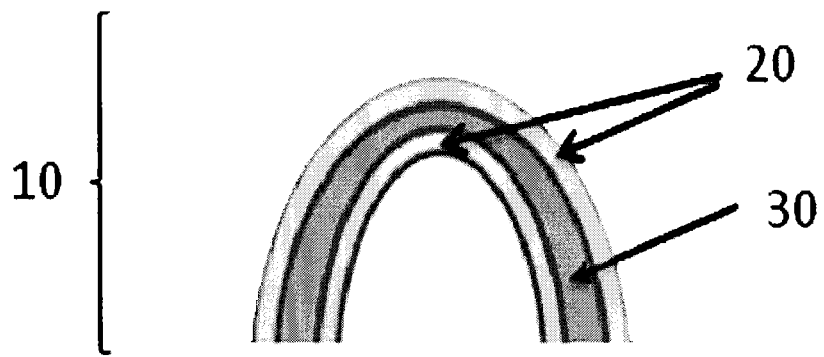
FIG. 1 depicts an example of a dental tray which is utilized on either the upper teeth and jaw or the lower teeth and jaw.
Figure 1:
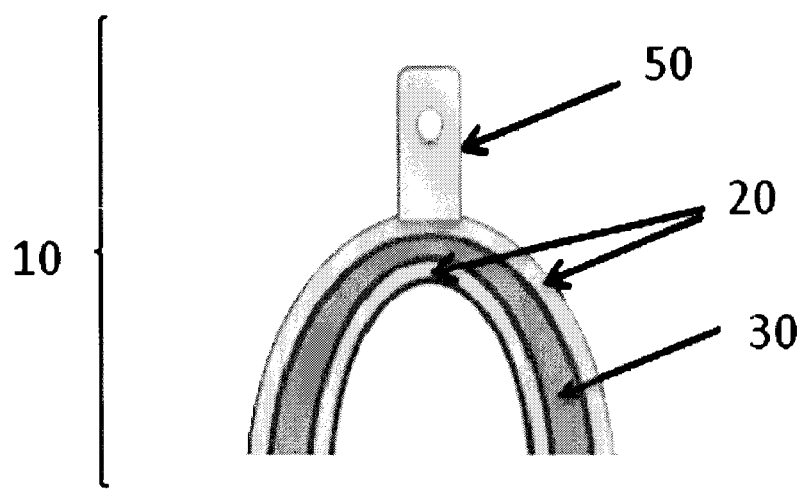

It is important to draw a clear distinction between the previous silicone resins employed for dental impressions and other applications as described in U.S. Patent Application Publication US2007/0134618 A1, European application EP 0 522 341 A1 and PCT application WO 93/17654 and those of the present invention. The aforementioned compositions differ from those of the present invention in two important respects. First, the aforementioned compositions contain surfactants that are necessary to modify the wetting properties of the silicone resin for dental impressions. These surfactants are not required in the present invention. Secondly, and most significantly, the cured silicone resin formulations of the present invention achieve the desired mechanical properties of toughness and tear resistance without the need for highly vinyl functional QM resins specified in the prior art.

QM resins are well-known in the art and follow a recognized nomenclature. The generally accepted definitions for M, D, T and Q (found on page 3 of Chemistry and Technology of Silicones by Walter Noll, Academic Press, New York, 1968) are the ones used herein. They are described in the following Table 1:

TABLE 1

STRUCTURAL UNITS OF THE POLYORGANOSILOXANES (Silicones)

| Structural formula | Composition | Functionality | Symbol |
|---|---|---|---|
| R—Si(R)(R)—O— | $R_3SiO_{1/2}$ | Monofunctional | M |
| —O—Si(R)—O— (with R) | $R_2SiO_{2/2}$ | Difunctional | D |
| —O—Si(R)—O— (with O) | $RSiO_{3/2}$ | Trifunctional | T |
| —O—Si(O)—O— (with O) | $SiO_{4/2}$ | Tetrafunctional | Q |

The R groups are organo groups that are joined to silicon by means of a carbon-silicon bond. Thus, the Q units, also known as "quaternary" units are repeat units in the silicone polymer structure that contain no carbon-silicon bonds. These units serve as tetrafunctional groups that often are used to provide branches and crosslinks in network silicone polymers. The monomers, oligomers and polymers of the present invention do not contain Q units except to the extent that they may exist as impurities in the intended monomers, oligomers and polymers.

The term "dental", for purposes of this application, relates to anything in or related to the oral cavity. This may include the teeth, gums, tongue or interior surfaces of the lips. It may also refer to the jaw as it relates to jaw positioning.

Unless the resin is further described or modified, the term "resin", for purposes of this application, refers to the prepolymerized mixture.

Silicone Resin

The silicone resin consists of two components. Component A of the silicone resin consists of:
1. a nano-particulate silica-filled vinyl-functional poly(dimethylsiloxane),
2. an optional linear, branched or cyclic vinyl functional compound or poly(dimethylsiloxane), and
3. a platinum catalyst.

Component B of the silicone resin consists of:
1. a nano-particulate silica-filled vinyl-functional poly(dimethylsiloxane) and
2. a linear, branched or cyclic Si—H functional poly(dimethylsiloxane).

Part 1 in Component A is a nano-particulate silica filled vinyl-functional poly(dimethylsiloxane) with a vinyl content ranging from approximately 0.02 to 0.08 mmol/g. The density ranges from approximately 0.95 to 1.2 g/cc. Part 1 in Component A may be formulated by intensive high shear blending of a vinyl-functional poly(dimethylsilxoane) resin with fume nano-particulate silica that has been surface treated with cyclic dimethylsiloxanes or other coupling agents known in the art. Sufficient polydisperse silica with a particle size range between approximately 5 nm to 50 nm is added to provide a viscosity of from about 250,000-1,500,000 cps to the first component. Polydisperse silica is better able to impart viscosity than is monodisperse silica, which is typically used in applications in which increased viscosity is not desired. Alternatively, commercially available preblended silica filled vinyl-functional poly(dimethylsiloxane) is available and can be used directly in this invention. In some embodiments, the silica filled vinyl-functional poly(dimethylsiloxane) comprises 90-99.5% by weight of Component A. In other embodiments, the silica filled vinyl-functional poly (dimethylsiloxane) comprises approximately 91-99.4% by weight of Component A. In other embodiments, the silica filled vinyl-functional poly(dimethylsiloxane) comprises 98-99.4% by weight of Component A.

A stabilizer is often, but not always, required in crosslinkable silicone resins that cure by means of a hydrosilation reaction. The function of the stabilizer is to control the rate of cure. Part 2 in Component A, when present, serves this purpose. In some embodiments of the invention, the stabilizer is a linear, branched or cyclic vinyl-functional poly(dimethylsiloxane) having from 2 to 5 vinyl groups per molecule. The stabilizer may be selected from the group including, but not limited to: 1,3-divinyltetramethyldisiloxane; 1,5-divinylhexamethyltrisiloxane; 1,3,5-trivinylpentamethyltrisiloxane; 1,3,5-trivinylcyclotrisiloxane; 1,3,5,7-tetravinylcyclotetrasiloxane and 1,3,5,7,9-pentavinylcyclopentasiloxane. In some embodiments of the invention, the stabilizer is 1,3-divinyltetramethyldisiloxane. In some embodiments of the invention in which stabilizer is present, the amount of stabilizer required is from 0.05-5% of the total prepolymer mixture. In other embodiments, the amount of stabilizer present ranges from 0.1-1.0% of the total prepolymer mixture. In still other embodiments, the amount of stabilizer present ranges from 0.1-0.6% of the total prepolymer mixture. In yet other embodiments, there is no stabilizer present. The cure time is highly sensitive to the amount of stabilizer and small amounts can be used to extend the handling time prior to insertion of the dental appliance into the oral cavity.

In Component A, part 3 is a platinum-containing hydrosilation catalyst. As noted below, a variety of different platinum compounds and complexes can be used for this purpose. The amount of complex required varies widely with their activity. Generally, it has been found sufficient platinum compound or complex is required to afford 0.001-0.01 g platinum metal per 20 g of total silicone resin to provide a cure time under 7 minutes at physiological temperature (approx. 37° C.). In some embodiments of the invention, the amount of platinum metal is 0.002-0.008 g per 20 g of total silicone resin. In other embodiments, the amount of platinum metal is 0.002-0.004 g per 20 g of total silicone resin. In still other embodiments, the amount of platinum metal is 0.001-0.003 g per 20 g of total silicone resin.

The nano-particulate silica filled vinyl-functional poly (dimethylsiloxane) used in Part 4 of Component B may be the same as in part 1 of Component A, but is not required to be. In some embodiments of the invention, the amount of Part 4 comprises 74-97% by weight of Component B. In other embodiments, the amount of Part 4 comprises 85-94% by weight of Component B.

Part 5 of Component B is a linear, branched or cyclic organohydrofunctional polysiloxane (Si—H functional poly (siloxane)) bearing pendant and terminal Si—H functional groups with a viscosity of 40-300 cps and a Si—H content ranging from 1.4-5.0 mmol/g. In one embodiment of the invention, part 5 consists of a linear or branched poly(dimethylsiloxane) with a minimum Si—H functionality of 2 for a linear moiety and 3 or more if it is branched. In another embodiment, part 5 is a cyclic Si—H functional siloxane. Examples of part 5 include, but are not necessarily limited to 1,3,5-trimethylcyclotrisiloxane, 1,3,5,7-tetramethylcyclotetrasiloxane, 1,3,5,7,9-pentamethylcyclopentasiloxane, tetrakis(dimethylsiloxy)silane, tris(dimethylsiloxy)methylsilane, UXlink 140 and UXlink 430 (both UXlink supplied by Momentive Performance Materials). In some embodiments of the invention, part 5 comprises 3-26% by weight of Component B. In other embodiments of the invention, part 5 comprises 6-15% by weight of Component B. In still other embodiments of the invention, part 5 comprises 4-10% by weight of Component B.

In the invention, the cross-linkable, vinyl-functional poly (dimethylsiloxane)s of Component A and Component B are both substantially free of vinyl functional silicone monomers, oligomers or polymers containing quaternary silicon-oxygen bonded repeat units. Additionally, as mentioned supra, the resin is substantially free of surfactant. "Substantially free of" as used herein means containing either none of the named component or so little as not to affect the physical properties. Generally this will be less than 1%, preferably less than 0.1%, and more preferably less than 0.01%.

The above Components A and B are designed to be combined and cured as 1:1 (by weight or volume) mixtures. As such they are suitable for application using commercially available double syringe packages. Mixing is provided by attachment of the double syringe to a static mixing head. Typically, the double syringe package and static mixing head are fabricated from various plastics with a new static mixing head employed for each use.

The above classes of two-component crosslinkable silicone resins are suitable for dental applications because they undergo reaction without the formation of byproducts. This reaction proceeds at room temperature and is not substantially affected by the presence of water or other agents commonly encountered in the oral cavity. Additional attributes that contribute to the suitability of these resins in dental applications are their lack of taste, smell and overall physiological inertness. Further, the above described resin compositions are highly viscous and, due to the presence of the nano-particulate filler, display a high degree of thixotropy. This means that they can be dispensed as fluids but behave as physical gels. Thus, they do not flow appreciably under their own weight. In the present application, this means that the resins can be dispensed into the aforementioned trays and will remain in place within the trays prior to and during application. The filled trays can subsequently be handled and conveniently used by the dentist, dental technician or patient himself to fabricate the final device by insertion into the oral cavity.

While the inventors do not wish to be limited by theory, it is generally held that the hydrosilation reaction process described above used in the two-component crosslinkable silicone resin is mediated by a noble metal catalyst. Typical catalysts used in this reaction are platinum compounds and platinum complexes although it is well known in the art that a variety of other catalysts, for example, rhodium and palladium complexes can also be employed. Among the many platinum-containing catalysts that can be used in this invention are the well known Speier (J. L. Speier, Advances in Comprehensive Organometallic Chemistry, Vol. 2, eds. G. Wilkinson, F. G. A. Stone and E. W. Abel, Pergamon, Oxford, 1982, pp. 117-120), Karstedt (U.S. Pat. No. 3,715,334), Ashby (U.S. Pat. No. 3,715,334) and Lamoreaux (U.S. Pat.

No. 3,220,972) catalysts and chloroplatinic acid ($H_2PtCl_6$), $Cl_2(COD)Pt(II)]_2$, $[Cl(COD)Pt(I)]_2$ and $Cl_2[(C_2H_5)_2S]_2Pt$ (II). The hydrosilation reaction and catalysts used in carrying it out are well known in the art.

Each of the above described components that make up the crosslinkable silicone resin is shelf stable under normal storage conditions at room temperature. Cure commences on mixing the two components together. This is most conveniently achieved within a dental setting through the use of a specially designed double barrel syringe that is mated with a detachable static mixing head. Depression of the dual syringe (usually with the aid of dispensing gun) delivers the two components in predetermined (herein 1:1) proportions to the static mixing head. Forcing the liquid components through the static mixing head provides an intimate, homogeneously combined mixture while simultaneously initiating the hydrosilation cure reaction. In most applications, the orifice end of the static mixing head is positioned so that it fills the applicator tray. Several alternative methods can also be employed to combine the two components of the silicone resin. For example, the two components can be simply combined in the proper proportions by volume or weight and hand mixed. The mixture can subsequently be conveyed to the tray by various means and the assembly inserted into the oral cavity for cure.

As previously mentioned, a tough but compliant cured silicone resin is required for all of the dental appliance applications discussed herein. These mechanical properties are largely determined by the character and proportions of the various constituents present in Components A and B. A number of different formulations will be described in the Examples that achieve this objective. Although we do not wish to be limited by theory, we have achieved the requisite mechanical characteristics by designing silicone resins filled with nano-particulate silica and possessing a specific crosslink density.

It is an objective of this invention to provide said silicone resins with a cure time acceptable to both ordinary dental practice and with consideration for dental patient comfort. An acceptable length of time for curing may be different for each patient: one patient may be willing to wait for 30 minutes for the resin to cure, while another may only be comfortable for 10 minutes. A cure time of seven minutes or less at approximately 37° C. is believed to be tolerable for most patients. The cure time is controlled by both the concentration of vinyl and Si—H (hydrosilane) groups present in the silicone precursors and by the level of the platinum catalyst employed for cure. Examples are provided that demonstrate control over this parameter of the cure.

Tray Design and Materials

Figure 2:
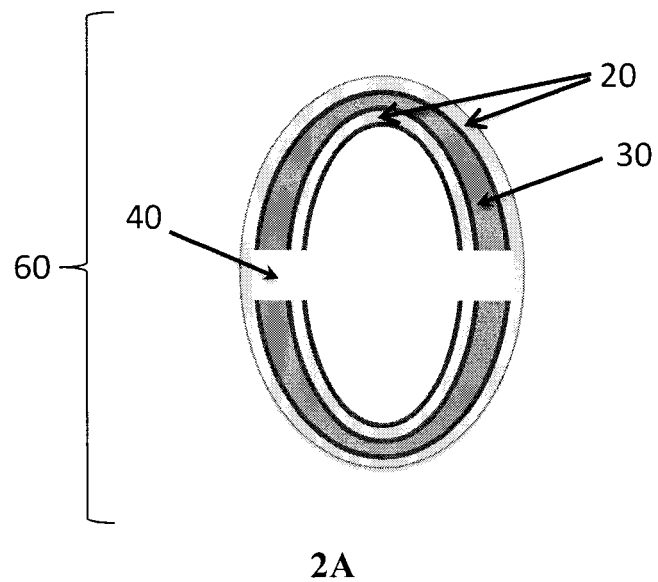
FIG. 2 depicts an example of a dental tray which is utilized on both the upper and lower teeth and jaw.
Figure 2:
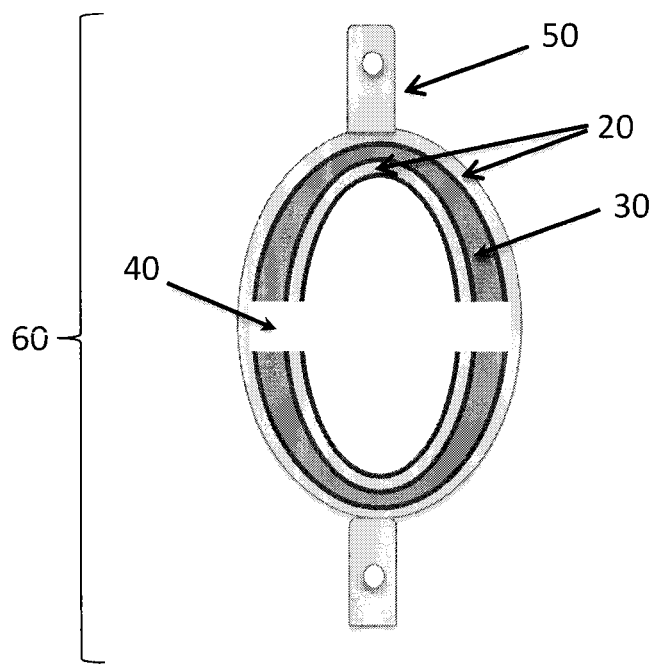

As previously indicated, an embodiment of this invention includes the tray in which the curable silicone resin is placed. The tray serves the function of providing a means for containing the uncured silicone resin and conveying it to the oral cavity. It is also designed to confine the resin to specific regions within the oral cavity. Further, after cure the tray becomes an integral part of the completed dental appliance. In most cases, the tray will consist of a thin plastic shell [20] containing an arch-shaped channel [30] that closely parallels the contour of the teeth in the jaw. This channel is where the silicone resin is added. FIGS. 1A and 1B show the configuration of one potential tray configuration. In this case, the tray [10] is designed to fit the teeth (and, depending on the application, the gums) of either the upper jaw or the lower jaw. Two trays of the type shown in FIG. 1 can be used to fit the teeth (and optionally the gums) of both jaws. In such a case, first one half of the jaw is fitted and cured with a tray as shown in FIG. 1, and then the second half is treated similarly with another tray as shown in FIG. 1. Alternatively, as shown in FIGS. 2A and 2B, a double tray [60] can be employed in which the teeth (and optionally the gums) of both the upper and lower jaws can be fitted simultaneously. In this case, an optional hinge [40] may be utilized in the tray to improve patient comfort during tray placement.

The tray optionally may be fitted with specially designed tabs [50] to assist in insertion and withdrawal from the oral cavity before and after curing as well as during repeated use of the dental appliance.

The tray may be constructed from rigid or flexible thermoplastic resins by a number of conventional molding techniques including but not limited to: injection molding, compression molding or by vacuum sheet or pressure forming. Some typical thermoplastic resins that can be used for this purpose include poly(ethylene), poly(propylene), poly(methylmethacrylate), poly(oxymethylene), poly(carbonate), poly(styrene), poly(butylene terephthalate), poly(ethylene terephthalate), poly(acrylonitrile)-poly(butadiene)-poly(styrene) copolymer, high impact poly(styrene), nylon-6, nylon-6,6, nylon-6,12, among many others.

The tray may be fabricated from clear (unfilled) or filled thermoplastic resins and may also contain pigments, dyes, and/or other processing aids.

In some embodiments, it is desirable that the cured silicone resin adhere to the tray to provide an integrally bonded dental appliance. In many cases, sufficient bond strength will be achieved during curing of the silicone resin within the tray. However, bonding may also be augmented by other means. For example, the surface of the tray in contact with the silicone resin may be textured during fabrication or roughened by abrasion or etching afterwards. Alternatively or additionally, various coupling agents may be used to treat the surface of the tray to promote bonding. Examples of applicable coupling agents comprise but are not limited to: alkyl trialkoxysilanes, dialkyl dialkoxysilanes, alkyl triacetoxysilanes and titanium tetraalkoxides. It may be advantageous to employ both techniques to ensure bonding of the silicone resin to the tray. Another technique for improving bonding is to employ flame or corona ionization of the surface of the tray. In addition, the channel of the tray may be perforated to allow a further avenue for attaching and integrating the cured silicone to the tray.

The design of the tray configuration will be tailored to the specific dental appliance application for which it is intended. For example, night guard trays will have a different design than those employed for sporting mouth guards and these will again be differently configured from dental appliances designated for use as temporal-mandibular jaw splints. It is envisioned that a number of different tray sizes for each dental appliance application will be required to accommodate the requirements of various adult and juvenile patients.

The procedure for the fabrication of a dental appliance consists of combining the Components A and B of the silicone resin using either
1. manual dispensing and hand mixing;
2. a double syringe coupled to a disposable static mixer; or
3. a pressure activated automated dual delivery system equipped with a static mixing head.

Methods 2 and 3 are preferred since they do not introduce excessive amounts of air which may become trapped during cure of the silicone resin.

Once the silicone resin is delivered to the tray, the assembly is then introduced into the oral cavity and positioned both by the dental personnel and by the patient's opposing jaw. The patient is then asked to bite down on the tray. With the patient holding the bite, the resin sets or hardens. The finished dental appliance is then removed from the oral cavity and examined for any defects. Some trimming and/or polishing may be necessary to remove any excess gelled resin and tray material. The result is a well-adapted, economical, comfortable, long lasting dental device.

In some embodiments, the invention may further comprise a dental medicament. Such medicaments include, but are not limited to, one or more of a tooth-whitening bleach, fluoride, an anti-bacterial agent or an oxidizing agent. The conformal nature of the crosslinkable silicone resin used in this technology ensures that therapeutic agents (bleach, antibacterial agents, etc.) will be held in close contact with the teeth and/or gums for extended time periods to deliver their activity to the targeted teeth or periodontal pockets. The chemically inert nature of the silicone resin used in this technology ensures that neither the device nor the potency of the therapeutic agent will be degraded during the treatment; for instance, the present invention provides a conformal tray that is inert to bleaching agent and that can hold a bleaching agent in direct contact with the teeth. Further, the silicone appliances described in this invention are transparent to UV light and can be used in a photo-assisted bleaching process. In a similar fashion, the custom-fit dental appliances can be used for other therapeutic uses, such as to deliver fluoride or to protect sensitive gums after dental surgery.

A second way in which the devices of this invention can be used in the treatment of periodontal disease is to incorporate dental medicaments, such as, but not limited to, active anti-bacterial agents (for example, streptomycin), into the silicone resin used to fabricate the device. When the patient wears the device, the medicament will be slowly leached from the device and will be delivered to the treatment sites within the oral cavity.

In addition to periodontal disease, dental caries and sensitivity, cure and prevention can also be carried out by the use of oral trays of this invention filled with anti cavity chemicals, particularly fluoride, to help decrease bacteria and strengthen teeth. The new tray fabrication technique and materials described herein will help keep all prevention medications in closer contact with tooth surfaces than the trays in current use, thus enhancing the effectiveness of all desensitizing and decay prevention techniques.

The incorporation of dyes, pigments or other inert colorants into one or both of the components of the silicone resin may be desirable for esthetic purposes, for personal identification of the dental appliance or for inspection purposes. Such agents are within the scope and intent of the present invention.

While night guards, mouth guards, bleaching trays and trays for treatment of periodontal disease constitute the prime applications of the novel dental appliances described in this invention, they are not the exclusive objectives. Additional applications include but are not limited to: anti-snoring devices, temporal-mandibular jaw splints and teeth positioning devices. In the latter case, the highly conformal yet resilient nature of the resin in the device can hold the alignment of teeth and prevent their movement. The comfort provided by these devices makes them highly suitable for use as dental retainers for night-time and long-term wear. An additional application for the silicone resin employed in this invention is as a temporary dental adhesive. The adhesive can be used to bond crowns and bridges in temporary restorations to existing and implanted dental structures and still be easily removed when desired. The material is also suitable to be used to provide a soft and comfortable lining in removable oral prostheses, i.e., full and partial dentures.

EXAMPLES

The following examples are not construed as limiting and are offered by way of illustration. The experiments described in these examples were carried out at room temperature (approx. 25° C.). For this reason, gel times in the oral cavity (approx. 37° C.) on actual dental appliances will be somewhat shorter.

Example 1

The following two-component mixture was prepared.
Component A
  1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
  2. 0.067 g Platinum-1,3-divinyltetramethyldisiloxane complex in vinyl terminated silicone oil (Gelest 91P6830.3) with a platinum content of 3.0-3.5%.
Component B
  1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
  2. 0.75 g UXlink 140 organohydrofunctional polysiloxane (Si—H functional poly(siloxane), Si—H content 1.4 mmol/g; viscosity 300 cps) (supplied by Momentive Performance Materials).

The individual parts of Components A and B were hand mixed together and then each component was loaded into the separate barrel of a double barrel syringe. The dual plunger of the syringe was inserted and the assembly inverted to allow the entrapped air bubbles to escape. A static mixing head was affixed to the syringe and this was used to fill a transparent poly(methyl methacrylate) tray for a night guard. Thereafter, the tray was inserted into the oral cavity of a patient in such a manner that the teeth of the front portion of the upper jaw were encapsulated by the patient biting down on the tray. The time elapsed to this point in the process after dispensing the mixed silicone resin into the tray was approximately 0.5-1 minutes. After an additional 5 minutes, the silicone resin was set and was removed from the patient's mouth. The completed night guard was ready for immediate use.

Example 2

The following two-component mixture was prepared.
Component A
  1. 10 g Base Compound P-300 Nano-particulate silica filled vinyl functional silicone resin having a viscosity of 300,000 cps, a density of 1.1 g/ml and a vinyl content of 0.04 mmol/g
  2. 0.055 g 1,3-divinyltetramethyldisiloxane (supplied by Gelest Co.)
  3. 0.067 g Platinum-1,3-divinyltetramethyldisiloxane complex in vinyl terminated silicone oil (Gelest 91P6830.3) with a platinum content of 3.0-3.5%)
Component B
  1. 10 g Base Compound P-300 Nano-particulate silica filled vinyl functional silicone resin having a viscosity of 300,000 cps, a density of 1.1 g/ml and a vinyl content of 0.04 mmol/g.
  2. 0.75 g 1,3,5,7,9-pentamethylcyclopentasiloxane (supplied by PCR Inc.)

The parts of each of components A and B were separately mixed and then each part was loaded into a 12 mL syringe. To measure the cure time, two gram aliquots of Components A and B were weighed into a shallow dish and mixed. Gelation took place after one minute. A soft elastomeric non-tacky elastomer was obtained.

Example 3

The following two-component mixture was prepared.
Component A
1. 10 g Base Compound P-300 Nano-particulate silica filled vinyl functional silicone resin having a viscosity of 300,000 cps, a density of 1.1 g/ml and a vinyl content of 0.04 mmol/g.
2. 0.055 g 1,3-divinyltetramethyldisiloxane (supplied by Gelest Co.)
3. 0.067 g Platinum-1,3-divinyltetramethyldisiloxane complex in vinyl terminated silicone oil (Gelest 91P6830.3) with a platinum content of 3.0-3.5%)
Component B
10 g Base Compound P-300 Nano-particulate silica filled vinyl functional silicone resin having a viscosity of 300,000 cps, a density of 1.1 g/ml and a vinyl content of 0.04 mmol/g.
1. 0.75 g UXlink 430 organohydrofunctional polysiloxane (Si—H functional poly(siloxane)) (supplied by Momentive Performance Materials) having a Si—H content of 4.3 mmol/g and a viscosity of 40 cps.

The parts of each of components A and B were separately mixed and then each part was loaded into a 12 mL syringe. To measure the cure time, two gram aliquots of Components A and B were weighed into a shallow dish and mixed. Gelation took place after 3 minutes. A tough gelled elastomeric elastomer was obtained after 10 minutes that became non-tacky after an additional 2 minutes.

Example 4

The following two-component mixture was prepared.
Component A
1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
2. 0.055 g 1,3-divinyltetramethyldisiloxane (supplied by Gelest Co.)
3. 0.067 g Platinum-1,3-divinyltetramethyldisiloxane complex in vinyl terminated silicone oil (Gelest 91P6830.3) with a platinum content of 3.0-3.5%)
Component B
1. 10 g Base Compound P-300 Nano-particulate silica filled vinyl functional silicone resin having a viscosity of 300,000 cps, a density of 1.1 g/ml and a vinyl content of 0.04 mmol/g.
2. 0.34 g UXlink 430 organohydrofunctional polysiloxane (Si—H functional poly(siloxane)) (supplied by Momentive Performance Materials) having a Si—H content of 4.3 mmol/g and a viscosity of 40 cps.

The parts of each of components A and B were separately mixed and then each part was loaded into a 12 mL syringe. To measure the cure time, two gram aliquots of Components A and B were weighed into a shallow dish and mixed. Gelation took place after 9 minutes. The formulation remained tacky even after standing for 15 minutes.

Example 5

The following two-component mixture was prepared.
Component A
1. 10 g Base Compound P-1300 Nano-particulate silica filled vinyl functional silicone resin having a viscosity of 1,300,000 cps, a density of 1.15 g/ml and a vinyl content of 0.04 mmol/g (supplied by Momentive Performance Materials).
2. 0.055 g 1,3-divinyltetramethyldisiloxane (supplied by Gelest Co.)
3. 0.067 g Platinum-1,3-divinyltetramethyldisiloxane complex in vinyl terminated silicone oil (Gelest 91P6830.3) with a platinum content of 3.0-3.5%)
Component B
1. 10 g Base Compound P-1300 Nano-particulate silica filled vinyl functional silicone resin having a viscosity of 1,300,000 cps, a density of 1.15 g/ml and a vinyl content of 0.04 mmol/g.
2. 0.75 g UXlink 140 organohydrofunctional polysiloxane (Si—H functional poly(siloxane), Si—H content 1.4 mmol/g; viscosity 300 cps) (supplied by Momentive Performance Materials)

The parts of each of components A and B were separately mixed and then each part was loaded into a 12 mL syringe. To measure the cure time, two gram aliquots of Components A and B were weighed into a shallow dish and mixed. Gelation required over 15 minutes.

Example 6

The following two-component mixture was prepared.
Component A
1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
2. 0.055 g 1,3-divinyltetramethyldisiloxane (supplied by Gelest Co.)
3. 0.067 g Platinum-1,3-divinyltetramethyldisiloxane complex in vinyl terminated silicone oil (Gelest 91P6830.3) with a platinum content of 3.0-3.5%)
Component B
1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
2. 1.5 g UXlink 140 organohydrofunctional polysiloxane (Si—H functional poly(siloxane), Si—H content 1.4 mmol/g; viscosity 300 cps) (supplied by Momentive Performance Materials)

The parts of each of components A and B were separately mixed and then each part was loaded into a 12 mL syringe. To measure the cure time, two gram aliquots of Components A and B were weighed into a shallow dish and mixed. This formulation required 11 minutes for gelation.

Example 7

The following two-component mixture was prepared.
Component A
1. 10 g Base Compound P-300 Nano-particulate silica filled vinyl functional silicone resin having a viscosity of 300,000 cps, a density of 1.1 g/ml and a vinyl content of 0.04 mmol/g.

2. 0.025 g 1,3-divinyltetramethyldisiloxane (supplied by Gelest Co.)
3. 0.067 g Platinum-1,3-divinyltetramethyldisiloxane complex in vinyl terminated silicone oil (Gelest 91P6830.3) with a platinum content of 3.0-3.5%)

Component B
1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
2. 1.0 g UXlink 140 organohydrofunctional polysiloxane (Si—H functional poly(siloxane), Si—H content 1.4 mmol/g; viscosity 300 cps).

The parts of each of components A and B were separately mixed and then each part was loaded into a 12 mL syringe. To measure the cure time, two gram aliquots of Components A and B were weighed into a shallow dish and mixed. This formulation required 7 minutes for gelation.

Example 8

The following two-component mixture was prepared.
Component A
1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
2. 0.025 g 1,3-divinyltetramethyldisiloxane.
3. 0.067 g Platinum-1,3-divinyltetramethyldisiloxane complex in vinyl terminated silicone oil (Gelest 91P6830.3) with a platinum content of 3.0-3.5%)

Component B
1. 10 g Base Compound P-300 Nano-particulate silica filled vinyl functional silicone resin having a viscosity of 300,000 cps, a density of 1.1 g/ml and a vinyl content of 0.04 mmol/g.
2. 0.50 g UXlink 140 organohydrofunctional polysiloxane (Si—H functional poly(siloxane), Si—H content 1.4 mmol/g; viscosity 300 cps).

The parts of each of components A and B were separately mixed and then each part was loaded into a 12 mL syringe. To measure the cure time, two gram aliquots of Components A and B were weighed into a shallow dish and mixed. This formulation required 14 minutes for gelation.

Example 9

The following two-component mixture was prepared.
Component A
1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
2. 0.067 g Platinum-1,3-divinyltetramethyldisiloxane complex in vinyl terminated silicone oil (Gelest 91P6830.3) with a platinum content of 3.0-3.5%)

Component B
1. 10 g Base Compound P-300 Nano-particulate silica filled vinyl functional silicone resin having a viscosity of 300,000 cps, a density of 1.1 g/ml and a vinyl content of 0.04 mmol/g.
2. 0.75 g UXlink 140 organohydrofunctional polysiloxane (Si—H functional poly(siloxane), Si—H content 1.4 mmol/g; viscosity 300 cps).

The parts of each of components A and B were separately mixed and then each part was loaded into a 12 mL syringe. To measure the cure time, two gram aliquots of Components A and B were weighed into a shallow dish and mixed. This formulation required 1.5 minutes for gelation.

Example 10

The following two-component mixture was prepared.
Component A
1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
2. 0.067 g Platinum-1,3-divinyltetramethyldisiloxane complex in vinyl terminated silicone oil (Gelest 91P6830.3) with a platinum content of 3.0-3.5%)

Component B
1. 10 g Base Compound P-300 Nano-particulate silica filled vinyl functional silicone resin having a viscosity of 300,000 cps, a density of 1.1 g/ml and a vinyl content of 0.04 mmol/g (supplied by Momentive Performance Materials)
2. 1.5 g UXlink 140 organohydrofunctional polysiloxane (Si—H functional poly(siloxane), Si—H content 1.4 mmol/g; viscosity 300 cps) (supplied by Momentive Performance Materials)

The parts of each of components A and B were separately mixed and then each part was loaded into a 12 mL syringe. To measure the cure time, two gram aliquots of Components A and B were weighed into a shallow dish and mixed. This formulation required 1.5 minutes for gelation and was tack-free after 4 minutes. A tough, resilient silicone elastomer was obtained.

Example 11

The following two-component mixture was prepared.
Component A
1. 10 g Base Compound P-1300 Nano-particulate silica filled vinyl functional silicone resin having a viscosity of 1,300,000 cps, a density of 1.15 g/ml and a vinyl content of 0.04 mmol/g (supplied by Momentive Performance Materials).
2. 0.067 g Platinum-1,3-divinyltetramethyldisiloxane complex in vinyl terminated silicone oil (Gelest 91P6830.3) with a platinum content of 3.0-3.5%)

Component B
1. 10 g Base Compound P-1300 Nano-particulate silica filled vinyl functional silicone resin having a viscosity of 1,300,000 cps, a density of 1.15 g/ml and a vinyl content of 0.04 mmol/g.
2. 0.75 g UXlink 140 organohydrofunctional polysiloxane (Si—H functional poly(siloxane), Si—H content 1.4 mmol/g; viscosity 300 cps) (supplied by Momentive Performance Materials)

The parts of each of components A and B were separately mixed and then each part was loaded into a 12 mL syringe. To measure the cure time, two gram aliquots of Components A and B were weighed into a shallow dish and mixed. Gelation required over 2.1 minutes and was tack-free after 6 minutes.

Example 12

The following two-component mixture was prepared.

Component A
1. 10 g Base Compound P-1300 Nano-particulate silica filled vinyl functional silicone resin having a viscosity of 1,300,000 cps, a density of 1.15 g/ml and a vinyl content of 0.04 mmol/g (supplied by Momentive Performance Materials).
2. 0.013 g 1,3-divinyltetramethyldisiloxane.
3. 0.067 g Platinum-1,3-divinyltetramethyldisiloxane complex in vinyl terminated silicone oil (Gelest 91P6830.3) with a platinum content of 3.0-3.5%)

Component B
1. 10 g Base Compound P-1300 Nano-particulate silica filled vinyl functional silicone resin having a viscosity of 1,300,000 cps, a density of 1.15 g/ml and a vinyl content of 0.04 mmol/g.
2. 0.75 g UXlink 140 organohydrofunctional polysiloxane (Si—H functional poly(siloxane), Si—H content 1.4 mmol/g; viscosity 300 cps) (supplied by Momentive Performance Materials)

The parts of each of components A and B were separately mixed and then each part was loaded into a 12 mL syringe. To measure the cure time, two gram aliquots of Components A and B were weighed into a shallow dish and mixed. Gelation required over 5 minutes and was tack-free after 11 minutes. A tough, resilient elastomer was obtained.

A comparison of examples 1, 7 and 12 provides a comparison of the effect of the 1,3-divinyltetramethylsiloxane on the cure time of identical formulations. As can be seen, the cure time and handling time can be adjusted by varying the concentration of this component within the formulation.

The following process is one example of a method of producing an embodiment of the invention. The occlusal plane of a stone model (e.g., a fiber reinforced plaster of Paris) was built up with wax to make it flat. An alginate impression is taken and poured in stone. A variety of thermo-forming materials may be used, such as a hard tray material and a soft bleaching tray material in a range of thicknesses. When the appropriate material is chosen, the tray material is molded around the new flat stone model, for instance, by employing a pressure forming machine. The person of skill will realize that alternative methods may be used for making the tray. A high speed dental drill is then used to trim the flat section off the model to create the actual tray. The tray can be trimmed to extend as far back in the patient's mouth as desired; in one instance, the tray is trimmed to extend from the left first premolar to the right first premolar. The tray is then smoothed and polished to be comfortable for the patient, and retention grooves are drilled into the inside of the tray. The inside of the tray is then lined with the prepolymer resin and inserted into the patient's mouth. The patient is instructed to bite and stay biting while the material hardens, for instance, for ten minutes. Once fully hard, the tray is removed and the excess overflow of hard material is trimmed, for instance, by using laboratory scissors. The tray is then reinserted into the patient's mouth and the bite is checked and adjusted. Once the patient feels comfortable, he/she is sent home with instructions on when to wear their specific tray and with cleaning instructions.

Eight patients filled out questionnaires about the process of making and using the dental devices as described above. The patients were asked to rate the overall experience with the device and their experience with the making and fitting of the device (as described above) on a scale of 1 to 10, with 1 being "poor" and 10 being "excellent." The results are shown in Table I.

TABLE I

| Patient Number | Overall Experience with Product | Experience with Making and Fitting of Product |
|---|---|---|
| 1 | 2 | 5 |
| 2 | 7 | 7 |
| 3 | 10 | 10 |
| 4 | 10 | 10 |
| 5 | 7 | 9 |
| 6 | 10 | 10 |
| 7 | 8 | 8 |
| 8 | 10 | 10 |
| Average | 8.00 | 8.63 |
| Std. Dev. | 2.60 | 1.73 |

While several aspects of the present invention have been described and depicted herein, alternative aspects may be affected by those skilled in the art to accomplish the same objectives. Accordingly, it is intended by the appended claims to cover all such alternative aspects as fall within the true spirit and scope of the invention. Although this invention is susceptible to embodiment in many different forms, some preferred embodiments of the invention are shown. It should be understood, however, that the present disclosure is to be considered as an exemplification of the principles of this invention and is not intended to limit the invention to the embodiments illustrated.

We claim:

1. A resin substantially free of surfactant comprising:
   (a) a first component comprising
      (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said first component, said cross-linkable, vinyl-functional poly(dimethylsiloxane)s being substantially free of monomers containing quaternary silicon-oxygen bonded repeat units including QM resins; and
      (ii) a platinum catalyst; and
   (b) a second component comprising
      (i) a cross-linkable, vinyl-functional poly(dimethylsiloxane) having a vinyl content between 0.02 and 0.08 mmol/g and an amount of polydisperse silica of particle size 5 to 50 nm sufficient to impart a viscosity between 250,000 cps and $1.5 \times 10^6$ cps to said second component, said cross-linkable, vinyl-functional poly(dimethylsiloxane)s being substantially free of monomers containing quaternary silicon-oxygen bonded repeat units including QM resins; and
      (ii) a linear, branched or cyclic hydrofunctional poly(siloxane) having a Si—H content from 1.4 to 5.0 mmol/g and viscosity of 40-300 cps;
   wherein the platinum catalyst is the only catalyst in the resin; and
   wherein after the resin is cured, the resulting product is flexible and contours to the mouth and teeth of the patient for repeated withdrawal and reinsertion.

2. A resin according to claim 1 wherein said first component and said second component are present in a ratio by volume of approximately 1:1.

3. A resin according to claim 1 further comprising a dental medicament.

4. A resin according to claim 3, wherein said medicament is selected from the group consisting of a tooth-whitening bleach, fluoride, an anti-bacterial agent and an oxidizing agent.

5. A resin according to claim 1, wherein the first component further comprises a linear, branched or cyclic vinyl-functional poly(dimethylsiloxane) having from 2 to 5 vinyl groups per molecule.

6. A resin according to claim 1, wherein the linear, branched or cyclic vinyl-functional poly(dimethylsiloxane) is present in the range of 0.05%-5.0% by weight of the total resin.

* * * * *